(12) United States Patent
Marks et al.

(10) Patent No.: US 9,550,748 B2
(45) Date of Patent: Jan. 24, 2017

(54) CYCLIC CARBONATE MONOMERS AND POLYMERS PREPARED THEREFROM

(75) Inventors: Maurice J. Marks, Lake Jackson, TX (US); Allen S. Bulick, Lansdale, PA (US); Phillip S. Athey, Lake Jackson, TX (US); Dwight D. Latham, Clute, TX (US)

(73) Assignee: BLUE CUBE IP LLC, Midland, MI (US)

( * ) Notice: Subject to any disclaimer, the term of this patent is extended or adjusted under 35 U.S.C. 154(b) by 422 days.

(21) Appl. No.: 14/237,185

(22) PCT Filed: Jul. 19, 2012

(86) PCT No.: PCT/US2012/047329
§ 371 (c)(1),
(2), (4) Date: Feb. 5, 2014

(87) PCT Pub. No.: WO2013/028292
PCT Pub. Date: Feb. 28, 2013

(65) Prior Publication Data
US 2014/0191156 A1    Jul. 10, 2014

Related U.S. Application Data

(60) Provisional application No. 61/526,000, filed on Aug. 22, 2011.

(51) Int. Cl.
 C07D 317/36    (2006.01)
 C08G 71/04     (2006.01)
 C07D 317/40    (2006.01)

(52) U.S. Cl.
 CPC .......... *C07D 317/36* (2013.01); *C07D 317/40* (2013.01); *C08G 71/04* (2013.01)

(58) Field of Classification Search
 CPC .................................................. C07D 317/38
 See application file for complete search history.

(56) References Cited

FOREIGN PATENT DOCUMENTS

WO    WO 2008139315 A2 * 11/2008    ........... C07D 317/36

\* cited by examiner

*Primary Examiner* — Peter F Godenschwager
(74) *Attorney, Agent, or Firm* — Polsinelli PC

(57) ABSTRACT

A cyclic carbonate monomer including the reaction product of (a) a divinylarene dioxide, and (b) carbon dioxide; a process for making the cyclic carbonate monomer; and a polymer such as a poly(hydroxyurethane) composition made therefrom. The poly(hydroxyurethane) composition made from the above cyclic carbonate monomer forms a reactive intermediate that can be used for making, for example, a poly(hydroxyurethane) foam product.

16 Claims, No Drawings

CYCLIC CARBONATE MONOMERS AND POLYMERS PREPARED THEREFROM

FIELD

The present invention relates to novel cyclic carbonate monomers derived from divinylarene dioxides and carbon dioxide to provide reactive intermediates useful in the preparation of various polymer products.

BACKGROUND

Processes for preparing polymer products such as polyurethanes are known in the art. For example, traditional polyurethanes are synthesized by reacting an isocyanate with a polyol. Typical polyurethane foam formation via isocyanates is also known in the art. However, isocyanate-based polyurethane synthesis methods are known to have environmental, health and safety concerns and there is a growing trend in the industry to discover alternative chemistries to alleviate these concerns. Typically, isocyanate-based polyurethanes may be used, for example, in end-use applications such as spray foams.

It is also known to use a 1-12 part by weight addition of a mono alkyl cyclic carbonate as a stabilizer in traditional isocyanate foams; or as a blowing agent in traditional foam formulations. However, cyclic carbonate-amine foams per se are not known or taught in the prior art. In addition, nothing in the prior art teaches a divinylarene dioxide cyclic carbonate which can react at room temperature (25° C.) and produce an exotherm sufficient for room temperature cure and foam formation.

The polymerization of cyclic carbonates with amines is a known alternative to generating a related type of polyurethane network termed a poly(hydroxyurethane). But poly(hydroxyurethane)s derived from cyclic carbonates and amines suffer from poorer reactivity when compared to the aforementioned isocyanate chemistries. In addition, certain cyclic carbonate monomers, such as those derived from bisphenol A epoxy resins, are solids at room temperature, rendering processing difficult. Other cyclic carbonate monomers, such as those based on poly ether epoxy resins, remain liquid at room temperature but are not capable of room temperature cure or foam formation. In view of the above issues regarding cyclic carbonates with amines, foaming utilizing a cyclic carbonate monomer has heretofore not been disclosed in the prior art.

Heretofore, it known to prepare poly(hydroxyurethane)s by reacting a cyclic carbonate from an epoxy resin (e.g. bisphenol A diglycidyl ether) with a polyamine (e.g. diethylenetriamine, ethylene diamine). The resulting polymers are mixed with other polyamines, pigments and fillers in an aqueous solution with a commercial aqueous epoxy resin (e.g. Beckopox, VEP 2385) to form an automotive coating. The poly(hydroxyurethane) polymer requires heat to cure and is created in solvent prior to incorporation with the aqueous epoxy resin. Similar materials utilizing a tricyclic carbonate (e.g. trimethylolpropanetriglycidyl ether converted to the tri cyclic carbonate) as a crosslinker with a primary amine functional resin for electro deposition coatings have also been disclosed in the art.

Also known in the art is a method for using amine-terminated oligomers and cyclic carbonate/epoxy-terminated oligomers to create a hybrid network of urethane/epoxy-amine groups.

The prior art generally requires heated curing (curing temperatures generally between 70° C. and 120° C.) to utilize cyclic carbonate-amine poly(hydroxyurethane) networks in traditional coating applications. Many examples also require solvent-based polymerizations because many traditional epoxy resins will solidify as the percentage of epoxy groups converted to cyclic carbonate groups approaches 100% (e.g. DER™ 383 begins to solidify as the bulk cyclic carbonate concentration exceeds 70%). Epoxy resins that remain liquids at room temperature after 100% conversion to the cyclic carbonate (e.g. DER 736) do not produce an exotherm when reacted with amines preventing room temperature cure or foam formation.

SUMMARY

The present invention solves the problems of the prior art by providing a novel cyclic carbonate monomer which can be used in as a reactive intermediate for preparing various polymers.

One embodiment of the present invention is directed to a novel cyclic carbonate monomer comprising a reaction product of (a) at least one divinylarene dioxide; and (b) carbon dioxide forming a reactive intermediate reaction product. The reactive intermediate product can be useful in preparing various polymers such as poly(hydroxyurethane)s.

Another embodiment of the present invention is directed to a process for preparing the novel cyclic carbonate monomer described above by reacting (a) at least one divinylarene dioxide; and (b) carbon dioxide forming a reactive intermediate reaction product.

Still another embodiment of the present invention is directed to a poly(hydroxyurethane) composition prepared from the above novel cyclic carbonate monomer. Advantageously, utilizing the cyclic carbonate monomers of the present invention eliminates the need to use isocyanates in the production of poly(hydroxyurethane)s because of the aforementioned environmental, health and safety concerns. Another advantage of the present invention is that isocyanates react with water whereas cyclic carbonates do not react with water; thus, allowing use of the composition of the present invention in other applications such as water-based coatings.

Yet another embodiment of the present invention is directed to a process for preparing the poly(hydroxyurethane) composition described above. For example, divinylbenzene dioxide (DVBDO) when converted to a dicyclic carbonate (e.g. divinylbenzene dicyclic carbonate, DVBDCC) via incorporation of $CO_2$ is exothermic and exhibits an adiabatic temperature rise from room temperature to ~120° C. when reacted with polyfunctional amines (>2 amino groups/molecule) with low equivalent weight (<~50 g/eq) allowing for the creation of a poly(hydroxyurethane) foam. DVBDCC overcomes the limitations of the prior art by being sufficiently reactive and remaining a liquid at room temperature (cyclic carbonate concentration <75%) to create a rigid foam. DVBDCC may also be used as an initiator with other cyclic carbonate monomers that do not exhibit a stable exotherm of >70° C. at room temperature to create poly(hydroxyurethane) foams. The present invention novel cyclic carbonate monomer may also be useful in preparing poly(hydroxyurethane) applications for use as coatings, binders and adhesives.

DESCRIPTION

In its broadest scope, the present invention includes a cyclic carbonate monomer comprising the reaction product of: (a) at least one divinylarene dioxide; (b) carbon dioxide; and (c) a catalyst. The resulting cyclic carbonate monomer, a reactive intermediate reaction product, may be used to prepare a polymer resin composition or formulation such as a poly(hydroxyurethane) polymer.

In the present invention, component (a) a divinylarene dioxide such as divinylbenzene dioxide (DVBDO) may be used to prepare the cyclic carbonate monomer of the present invention. The divinylarene dioxides useful in the present invention, particularly those derived from divinylbenzene such as for example DVBDO, are class of diepoxides which have a relatively low liquid viscosity but impart higher heat resistance and rigidity in its derived thermosets than do conventional epoxy resins.

The divinylarene dioxide useful in the present invention may comprise, for example, any substituted or unsubstituted arene nucleus bearing two vinyl groups in any ring position. The arene portion of the divinylarene dioxide may consist of benzene, substituted benzenes, (substituted) ring-annulated benzenes or homologously bonded (substituted) benzenes, or mixtures thereof. The divinylbenzene portion of the divinylarene dioxide may be ortho, meta, or para isomers or any mixture thereof. Additional substituents may consist of $H_2O_2$-resistant groups including saturated alkyl, aryl, halogen, nitro, isocyanate, or RO— (where R may be a saturated alkyl or aryl). Ring-annulated benzenes may consist of naphthlalene, tetrahydronaphthalene. Homologously bonded (substituted) benzenes may consist of biphenyl, diphenylether.

The divinylarene dioxide used for preparing the composition of the present invention may be illustrated generally by general chemical Structures I-IV as follows:

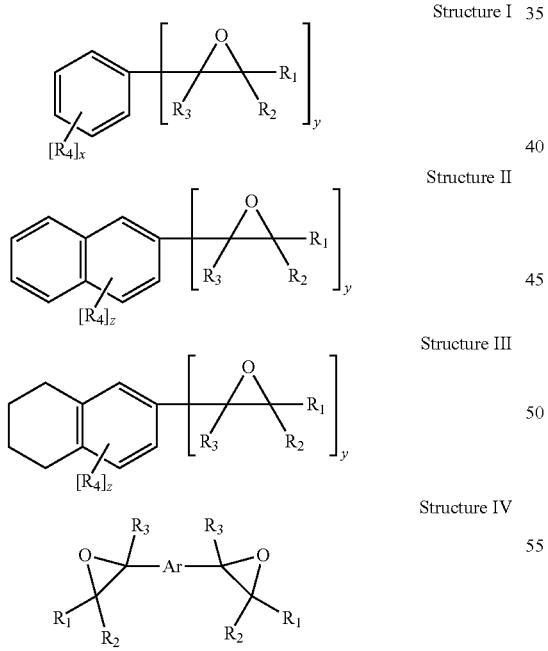

Structure I

Structure II

Structure III

Structure IV

In the above Structures I-IV of the divinylarene dioxide comonomer of the present invention, each $R_1$, $R_2$, $R_3$ and $R_4$ individually may be hydrogen, an alkyl, cycloalkyl, an aryl or an aralkyl group; or a $H_2O_2$-resistant group including for example a halogen, a nitro, an isocyanate, or an RO group, wherein R may be an alkyl, aryl or aralkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, 1,3-phenylene group.

In one embodiment, the divinylarene dioxide used in the present invention may be produced, for example, by the process described in U.S. Patent Provisional Application Ser. No. 61/141457, filed Dec. 30, 2008, by Marks et al. The divinylarene dioxide compositions that are useful in the present invention are also disclosed in, for example, U.S. Pat. No. 2,924,580.

In another embodiment, the divinylarene dioxide useful in the present invention may comprise, for example, divinylbenzene dioxide, divinylnaphthalene dioxide, divinylbiphenyl dioxide, divinyldiphenylether dioxide, and mixtures thereof.

In still another embodiment of the present invention, the divinylarene dioxide used in the epoxy resin formulation may be for example DVBDO. In yet another embodiment, the divinylarene dioxide component that is useful in the present invention includes, for example, a divinylbenzene dioxide as illustrated by the following chemical formula of Structure V:

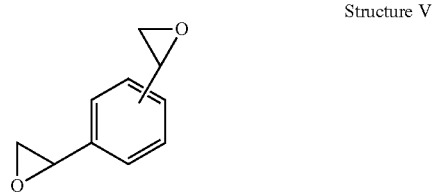

Structure V

The chemical formula of the above DVBDO compound may be as follows: $C_{10}H_{10}O_2$; the molecular weight of the DVBDO is 162.2; and the elemental analysis of the DVBDO is: C, 74.06; H, 6.21; and O, 19.73 with an epoxide equivalent weight of 81 g/mol.

Divinylarene dioxides, particularly those derived from divinylbenzene such as for example DVBDO, are class of diepoxides which have a relatively low liquid viscosity but a higher rigidity and crosslink density than conventional epoxy resins.

Structure VI below illustrates an embodiment of a chemical structure of the DVBDO useful in the present invention:

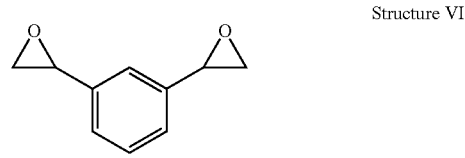 [SMILES: c1cc(C2CO2)cc(C2CO2)c1]

Structure VI

Structure VII below illustrates another embodiment of a chemical structure of the DVBDO useful in the present invention:

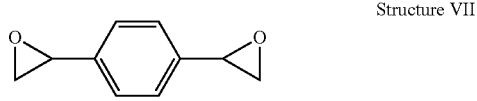 [SMILES: c1cc(C2CO2)ccc1C1CO1]

Structure VII

When DVBDO is prepared by the processes known in the art, it is possible to obtain one of three possible isomers: ortho, meta, and para. Accordingly, the present invention includes a DVBDO illustrated by any one of the above Structures individually or as a mixture thereof. Structures VI and VII above show the meta (1,3-DVBDO) isomer and the para (1,4-DVBDO) isomer of DVBDO, respectively. The ortho isomer is rare; and usually DVBDO is mostly produced generally in a range of from 9:1 to 1:9 ratio of meta (Structure VI) to para (Structure VII) isomers. The present invention includes as one embodiment a range of from 6:1 to 1:6 ratio of Structure VI to Structure VII, and in other embodiments the ratio of Structure VI to Structure VII may be from 4:1 to 1:4 or from 2:1 to 1:2.

In another embodiment of the present invention, the divinylarene dioxide may contain quantities (such as for example less than 20 weight percent) of substituted arenes. The amount and structure of the substituted arenes depend on the process used in the preparation of the divinylarene precursor to the divinylarene dioxide. For example, divinylbenzene prepared by the dehydrogenation of diethylbenzene (DEB) may contain quantities of ethylvinylbenzene (EVB) and DEB. Upon reaction with hydrogen peroxide, EVB produces ethylvinylbenzene monoxide while DEB remains unchanged. The presence of these compounds can increase the epoxide equivalent weight of the divinylarene dioxide to a value greater than that of the pure compound.

In one embodiment, the divinylarene dioxide, for example DVBDO, useful in the present invention comprises a low viscosity liquid epoxy resin (LER) composition. The viscosity of the divinylarene dioxide used in the process for making the epoxy resin composition of the present invention ranges generally from 0.01 Pascal-second (Pa-s) to 0.1 Pa-s in one embodiment, from 0.01 Pa-s to 0.05 Pa-s in another embodiment, and from 0.01 Pa-s to 0.025 Pa-s in still another embodiment, at 25° C. One of the advantageous properties of the divinylarene dioxides useful in the present invention is their thermal stability which allows their use in formulations or processing at moderate temperatures (for example, at from 100° C. to 200° C.) for up to several hours (for example, for at least 2 hours) without oligomerization or homopolymerization. Oligomerization or homopolymerization during formulation or processing is evident by a substantial increase in viscosity or gelling (crosslinking). The divinylarene dioxides useful in the present invention have sufficient thermal stability such that the divinylarene dioxides do not experience a substantial increase in viscosity or gelling during formulation or processing at the moderate temperatures.

Another advantageous property of the divinylarene dioxide useful in the present invention may be for example its rigidity. The rigidity property of the divinylarene dioxide is measured by a calculated number of rotational degrees of freedom of the dioxide excluding side chains using the method of Bicerano described in *Prediction of Polymer Properties*, Dekker, New York, 1993. The rigidity of the divinylarene dioxide used in the present invention may range generally from 6 to 10 rotational degrees of freedom in one embodiment, from 6 to 9 rotational degrees of freedom in another embodiment, and from 6 to 8 rotational degrees of freedom in still another embodiment.

The amount of divinylarene dioxide used to prepare the cyclic carbonate monomer of the present invention may include an equivalent ratio of the divinylarene dioxide to the carbon dioxide generally in the range of from 100:1 to 1:100 equivalent ratio in one embodiment, from 10:1 to 1:10 equivalent ratio in another embodiment, from 5:1 to 1:5 equivalent ratio in still another embodiment, and from 2:1 to 1:2 equivalent ratio in yet another embodiment, based on the equivalents of epoxide to moles of carbon dioxide.

Carbon dioxide ($CO_2$), component (b) of the present invention, may include a pure $CO_2$ compound or any mixtures that contain $CO_2$. $CO_2$ may be used as a solid, liquid, gaseous material or mixtures thereof.

The amount of carbon dioxide used to prepare the cyclic carbonate monomer of the present invention may include an equivalent ratio of the divinylarene dioxide to the carbon dioxide, based on the equivalents of epoxide to moles of carbon dioxide, as described above.

A wide variety of catalysts for the conversion of epoxides to cyclic carbonates are known to those skilled in the art. The catalysts may include, but are not limited to, quaternary ammonium salts, quaternary phosphonium salts, quaternary arsenium salts, and Lewis acids, for example organometallic catalysts such as chlorostannoxanes, and aluminum-salen complexes; and mixtures thereof. The catalyst may be supported or unsupported during synthesis.

The concentration of the catalyst used to prepare the cyclic carbonate monomer of the present invention may range generally from 0.1 wt % to 20 wt % in one embodiment; from 1 wt % to 10 wt % in another embodiment; and from 2 wt% to 5 wt% in still another embodiment.

Optional components useful in the present invention may include physical and/or chemical blowing agents, surfactants, solvents, fillers, plasticizers, fire retardant agents. The level for the optional component use in the composition of the present invention is formulation dependent. Generally, the level may be from 0.1 wt % to 75 wt %.

The preparation of the cyclic carbonate monomer of the present invention is achieved by contacting: a divinylarene dioxide, a carbon dioxide, a catalyst and other optional components; and then allowing the components to react under reaction conditions to produce the cyclic carbonate monomer.

Typically a catalyst may be added to the epoxy resin and $CO_2$ bubbles through under heating. However, there is no criticality in the order of mixing the components above. For example, a reactor may be charged with an epoxy resin and then $CO_2$ and a catalyst may be added simultaneously to the reactor.

The components are heated until the desired degree of conversion of epoxide groups to cyclic carbonate groups is achieved. The resulting product is allowed to cool to room temperature prior to or during isolation and is immediately usable in preparing a polymer such as poly(hydroxyurethane).

The reaction conditions to form the cyclic carbonate monomer include carrying out the reaction under a temperature, generally in the range of from 10° C. to 200° C. in one embodiment; from 60° C. to 150° C. in another embodiment; and from 100° C. to 150° C. in still another embodiment.

The pressure of the reaction may be from 0.1 bar to 20 bar in one embodiment; from 1 bar to 20 bar in another embodiment; and from 1 bar to 15 bar in still another embodiment.

For example, in one embodiment the cyclic carbonate monomer of the present invention may comprise the reaction product of a divinylarene dioxide, for example a divinylbenzene dioxide (DVBDO); and carbon dioxide. As a further illustration of one embodiment of the present invention, DVBDO may be reacted with $CO_2$ with an appropriate catalyst (such as for example tetraammonium salt) reacted at 100° C. under pressure.

The conversion of epoxide groups to cyclic carbonate groups may be from 1% to 100%. Applications requiring conditions suitable for neat cure may have a conversion from 1% to 80% in one embodiment; from 20% to 75% in another embodiment; and from 50% to 75% in still another embodiment. Viscosity may be controlled by control of the cyclic carbonate conversion.

The reaction process to prepare cyclic carbonate monomer of the present invention may be batch or continuous. The reactor used in the process may be any reactor and ancillary equipment well known to those skilled in the art.

An optional process useful in the present invention may include for example removing the catalyst used to prepare the cyclic carbonate by an extraction, absorption or recrystallization step.

The novel cyclic carbonate monomer compositions of the present invention comprise any substituted or unsubstituted arene nucleus bearing at least one cyclic carbonate group in any ring position. The arene portion of the cyclic carbonate monomer may consist of benzene, substituted benzenes, (substituted) ring-annulated benzenes or homologously bonded (substituted) benzenes, or mixtures thereof. The divinylbenzene portion of the divinylarene dioxide may be ortho, meta, or para isomers or any mixture thereof. Additional substituents may comprise saturated alkyl, aryl, halogen, nitro, isocyanate, epoxy or RO— (where R may be a saturated alkyl or aryl) groups. Ring-annulated benzenes may consist of naphthlalene, tetrahydronaphthalene. Homologously bonded (substituted) benzenes may consist of biphenyl, diphenylether.

The novel cyclic carbonate monomer compositions of the present invention may be illustrated generally by general chemical Structures VIII-XI as follows:

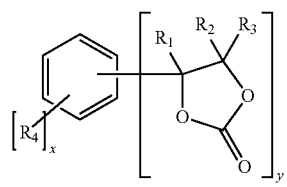

Structure VIII

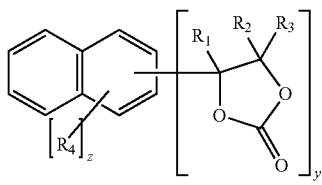

Structure IX

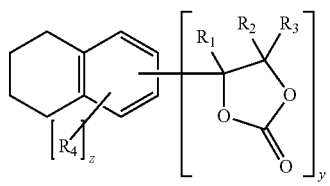

Structure X

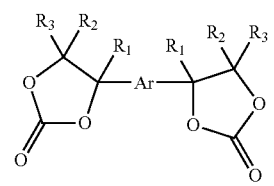

Structure XI

In the above Structures VIII-XI of the cyclic carbonate monomer of the present invention, each $R_1$, $R_2$, and $R_3$ individually may be hydrogen, an alkyl, cycloalkyl, an aryl or an aralkyl group; and each $R_4$ individually be hydrogen, an alkyl, cycloalkyl, an aryl or an aralkyl group, a halogen, a nitro, an ester, an epoxy or an RO group, wherein R may be an alkyl, aryl or aralkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, phenyl group. Structure XII represents a cyclic carbonate monomer of the present invention which contains an epoxide group bound to the aromatic ring, wherein $R_{1-3}$ are groups as defined above.

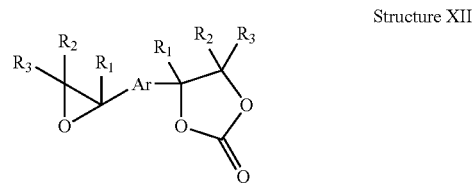

Structure XII

The novel cyclic carbonate monomer compositions of the present invention prepared as described above may range in viscosity from the viscosity of pure DVBDO to a solid at room temperature, depending on total conversion of epoxide groups. For applications requiring neat cure, viscosity may range from 0.01 Pa-s to 100 Pa-s; preferably from 0.01 Pa-s to 77 Pa-s; and most preferably from 0.01 Pa-s to 50 Pa-s. For applications which utilize a solvent to polymerize the monomer, any viscosity may be used.

The novel cyclic carbonate monomer composition of the present invention prepared as described above may be used for making various products such as for example an epoxy thermoset adhesive, coating, composite, or sealant; or a poly(hydroxyurethane) or poly(hydroxyurethane)/epoxy hybrid foam, coating, binder, adhesive, or sealant. Additionally, when the cyclic carbonate monomer composition of the present invention is reacted with a polyfunctional amine with an amine equivalent weight of ~24 g/eq, an adiabatic temperature rise from room temperature to 120° C. can be measured. For example, the same experiment with DVBDO yields no measurable temperature rise, indicating that cyclic carbonate monomers are more reactive than their epoxide counterparts. Cyclic carbonates may then be utilized in epoxy applications which require faster or lower temperature cure by converting a portion (e.g. 1% to 50%) of the epoxide groups to cyclic carbonates.

In one preferred embodiment, the novel cyclic carbonate monomer composition of the present invention may be useful in preparing polymers by reaction with a carbonate co-reactive monomer; for example, a poly(hydroxyurethane) by reaction with a polyamine, a poly(hydroxylthiourethane) by reaction with a polythiol, a poly(hydroxyester) by reaction with a polycarboxylic acid, and a poly(hydroxylether) by reaction with a polyol.

For example, a poly(hydroxyurethane) composition of the present invention includes the reaction product of (i) a cyclic carbonate monomer composition as described above; and (ii) a polyamine. For example, in one embodiment, a poly(hydroxyurethane) composition may be prepared by reacting: (i) the above described cyclic carbonate monomer; (ii)

at least one polyamine; and (iii) optionally, various additives under reaction conditions to form the poly(hydroxyurethane).

The first component (i) of the curable poly(hydroxyurethane) composition comprises the cyclic carbonate monomer described above such as DVBDCC.

Component (ii) useful for preparing the poly(hydroxyurethane) composition of the present invention may comprise any of the well known polyamines including for example triethylenetetraamine, ethylene diamine, diethylenetriamine, poly ether amines, for example polyamines sold under the trade name of Jeffamine® T-403 or Jeffamine® D-400, and mixtures thereof. Other amines useful in the present invention include for example aryl amines such as toluene diamine, methylene dianiline (including its polymeric homologs) and mixtures thereof.

The amount of carbonate co-reactive monomer used to prepare the cyclic carbonate monomer-based polymers of the present invention may include an equivalent ratio of the cyclic carbonate to the cyclic carbonate co-reactive monomer generally in the range of from 100:1 to 1:100 equivalent ratio in one embodiment, from 10:1 to 1:10 equivalent ratio in another embodiment, from 5:1 to 1:5 equivalent ratio in still another embodiment, and from 1.1:1 to 1:1.1 equivalent ratio in yet another embodiment, based on the equivalents of cyclic carbonate to co-reactive monomer.

In one preferred embodiment of the process for making a polymer includes reacting (a) a cyclic carbonate monomer compound; and (b) a carbonate co-reactive monomer, for example wherein the co-reactive monomer is a polyamine; and wherein the equivalent ratio of the cyclic carbonate monomer to the carbonate co-reactive monomer ranges from 10:1 equivalent ratio to 1:10 equivalent ratio.

Additives known useful for the preparation of poly(hydroxyurethane)s may be used as optional additional components, such as for example physical and/or chemical blowing agents, surfactants, solvents, fillers, plasticizers, fire retardant (FR) agents and mixtures thereof.

The concentration of the physical and/or chemical blowing agents used in the present invention should be sufficient to result in the desired density of the final article. The level of the blowing agent will be related to the moles of gas it will produce per total mass of the system (addition of amine, carbonate, and all additives). This may range generally from 0 moles of gas per kg of system to 10 moles of gas per kg of system in one embodiment, from 0.1 moles of gas per kg of system to 5 moles of gas per kg of system in another embodiment, from 0.1 moles of gas per kg of system to 2.5 moles of gas per kg of system in still another embodiment, and from 0.5 moles of gas per kg of system to 2.5 moles of gas per kg of system in yet another embodiment.

The concentration of the surfactants e used in the present invention may range generally from 0 wt % to 10 wt % in one embodiment, from 0.01 wt % to 5 wt % in another embodiment, from 0.1 wt % to 4 wt % in still another embodiment, and from 0.5 wt % to 3 wt % in yet another embodiment.

The concentration of the fillers used in the present invention may range generally from 0 wt % to 85 wt % in one embodiment, from 0.01 wt % to 75 wt % in another embodiment, from 0.1 wt % to 65 wt % in still another embodiment, and from 1wt % to 60 wt % in yet another embodiment.

The concentration of the plasticizers used in the present invention may range generally from 0 wt % to 50 wt % in one embodiment, from 0.01 wt % to 40 wt % in another embodiment, from 0.1 wt % to 30 wt % in still another embodiment, and from 1 wt % to 20 wt % in yet another embodiment.

The concentration of FR agents used in the present invention may range generally from 0 wt % to 50 wt % in one embodiment, from 0.01 wt % to 30 wt % in another embodiment, from 0.1 wt % to 20 wt % in still another embodiment, and from 1 wt % to 15 wt % in yet another embodiment.

The preparation of the poly(hydroxyurethane) composition of the present invention is achieved by reacting in a vessel the following components: (a) the cyclic carbonate or cyclic carbonate/epoxide hybrid monomer prepared as described above, (b) an amine, and optionally (c) a blowing agent and/or a surfactant; other epoxy resins (for example, aromatic and aliphatic glycidyl ethers, cycloaliphatic epoxy resins); other cyclic carbonate monomers; other curing agents; fillers; pigments; toughening agents; flow modifiers; adhesion promoters; and mixtures thereof, and then allowing the components to formulate into a poly(hydroxyurethane).

In one preferred embodiment, the process for making a cyclic carbonate monomer of the present invention includes reacting (a) a divinylarene dioxide; and (b) carbon dioxide, under conditions to provide cyclic carbonate monomer. In another embodiment, the process for making a cyclic carbonate monomer can include an epoxy resin, a reaction catalyst, or a combination thereof. The divinylarene dioxide can be selected from the group consisting of divinylbenzene dioxide, divinylnaphthalene dioxide, divinylbiphenyl dioxide, divinyldiphenylether dioxide, and mixtures thereof, preferably the divinylarene dioxide may be divinylbenzene dioxide. In addition, the mole ratio of the divinylarene dioxide to the carbon dioxide in the above process can range from 100:1 mole percent to 1:2 mole percent; and the process can be carried out at a temperature of from 50° C. to 200° C.

In general, there is no criticality to the order of mixture, i.e., the components of the reaction formulation or composition of the present invention may be admixed in any order to provide the poly(hydroxyurethane) reaction product of the present invention; for example in preparing a formulation for coatings. For certain other applications, such as for example for preparing a formulation for foams, it is preferred to premix component (a) with the blowing agent and surfactant followed by addition of component (b).

Any of the above-mentioned optional assorted formulation additives, for example a blowing agent, may also be added to the reaction mixture during the mixing or prior to the mixing to form the composition.

All the components of the cyclic carbonate monomer composition are reacted under conditions to form a poly (hydroxyurethane). For example, the reaction is carried out at a temperature enabling the preparation of a poly(hydroxyurethane) such as for example, generally from 0° C. to 200° C. in one embodiment, from 15° C. to 150° C. in another embodiment, and from 20° C. to 100° C. in still another embodiment.

The pressure of the reaction may be carried out, for example, at a pressure of 1 bar to 15 bar in one embodiment; from 1 bar to 10 bar in another embodiment; and from 1 bar to 3 bar in still another embodiment.

The reaction may be carried out, for example, for a predetermined period of time sufficient to cure the composition, defined as the point at which the desired cured properties are obtained. For example, the reaction time may be chosen between 5 seconds to 4 hours in one embodiment, between 10 seconds to 1 hour in another embodiment, and between 30 seconds to 30 minutes in still another embodiment.

The process to produce the poly(hydroxyurethane) products of the present invention may be performed by high pressure impingement mixing machine, impeller mixer or a static mixer. The foams could be sprayed, cast, injection molded or other ancillary equipment well known to those skilled in the art.

The poly(hydroxyurethane) polymer product of the present invention, prepared from the cyclic carbonate monomer described above, may have various beneficial and advantageous properties such as a high Tg, and fast cure compared to known poly(hydroxyurethane) compositions made from cyclic carbonate of the prior art.

The poly(hydroxyurethane) polymer product prepared as described herein may be used in various end uses including for example, foams, coatings, films, adhesives, binders, sealants, elastomers, laminates, composites, electronics, or castings.

The composition in another embodiment can be an aqueous dispersion made from one or more of the previously mentioned compounds.

In one embodiment, the poly(hydroxyurethane) is used for preparing for example a foam product.

The preparation of the poly(hydroxyurethane) foam material of the present invention is achieved by reacting in a vessel the following components: (A) the cyclic carbonate monomer prepared as described above; (B) a polyfunctional amine; (C) a blowing agent; (D) a surfactant; and (E) optionally one or more additives; and then allowing the components to formulate into a poly(hydroxyurethane) foam.

Component (A) used in preparing the poly(hydroxyurethane) foam material of the present invention is the cyclic carbonate monomer prepared as described above.

In preparing the poly(hydroxyurethane) foam material of the present invention one or more polyamines, component (B), such as triethylenetetramine (TETA), ethylene diamine (EDA) and diethylene triamine (DETA), can be used to produce a foam of the present invention.

In preparing the poly(hydroxyurethane) foam material of the present invention one or more blowing agents, component (C), can be used to produce a foam of the present invention. For example, physical or chemical blowing agents may be used. Physical blowing agents including for example hydrocarbons, fluorocarbons, hydrofluorocarbons, chlorocarbons, chlorofluorocarbons, hydrochlorofluorocarbons, water, inert gases, and mixtures thereof can be used. Chemical blowing agents which decomposed (activated) by heat to produce a gaseous product which then forms a foam product can also be used. For example, a known chemical blowing agent is azodicarbonamide.

Surfactants or foam stabilizers, component (D), can be useful for preparing a foam of the present invention. Any foam stabilizer known to useful by those of ordinary skill in the art of preparing polyurethane foams can be used with the present invention. Foam stabilizers useful for preparing a foam of the present invention may include for example, cationic surfactants, anionic surfactants, zwitterionic or a non-ionic surfactants, and mixtures thereof. Examples of anionic surfactants include sulfonates, carboxylates, and phosphates. Examples of cationic surfactants include quaternary amines. Examples of non-ionic surfactants include block copolymers containing ethylene oxide and silicone surfactants. Suitable silicone surfactants include for example commercially available polysiloxane/polyether copolymers.

The commericially available surfactants useful in the present invention include for example Tegostab B-8462 and B-8404 (Tegostab is a trademark of Goldschmidt Chemical Corp.); DC-198 and DC-5043 surfactants, available from Dow Corning; and L620 surfactants (Surfactant L620 is a polysiloxane surfactant available from Momentive).

In preparing the poly(hydroxyurethane) foam material of the present invention one or more additives may optionally be added to the composition. The optional additives may include for example, other epoxy resins (for example, aromatic and aliphatic glycidyl ethers, cycloaliphatic epoxy resins), other cyclic carbonate monomers, other curing agents, fillers, pigments, toughening agents, flow modifiers, adhesion promoters, FR agents, and mixtures thereof.

Generally, the amine containing component with the cyclic carbonate component is preferably added to the formulation last. The other required and optional components may be blended in either the amine side or carbonate side. There may be advantage to blend these components to give similar viscosity to facilitate the mixing.

All the components of the poly(hydroxyurethane) foam composition are reacted under conditions to form a poly(hydroxyurethane) foam. For example, the components described above are mixed at room temperature and the reaction proceeds due to spontaneous exotherm at a temperature enabling the preparation of a poly(hydroxyurethane) foam such as for example, generally from 50° C. to 200° C. in one embodiment, from 60° C. to 180° C. in another embodiment, and from 90° C. to 130° C. in still another embodiment.

The pressure of the reaction may be carried out, for example, at a pressure of 0.1 bar to 100 bar in one embodiment; from 0.5 bar to bar 10 in another embodiment; and from 0.8 bar to 2 bar in still another embodiment.

The foam reaction may be carried out, for example, for a predetermined period of time sufficient to cure the composition. For example, the foaming reaction time may be chosen between 0.1 minute to 48 hours in one embodiment, between 0.25 minutes to 12 hours in another embodiment, and between 0 5 minutes to 1 hour in still another embodiment.

The process to produce the poly(hydroxyurethane) foam of the present invention may be performed by high pressure impingement mixing machine, impeller mixer or a static mixer. The foams could be sprayed, cast, injection molded or other ancillary equipment well known to those skilled in the art.

In one embodiment, the amine component and the carbonate component are mixed well for example by using high shear impeller mixing or impingement of two high pressure streams.

The poly(hydroxyurethane) foam product of the present invention, prepared from the cyclic carbonate monomer described above, may have various beneficial and advantageous properties such as a high Tg, and fast curing compared to known poly(hydroxyurethane) foam products made from cyclic carbonates of the prior art. The poly(hydroxyurethane) foam product of the present invention also has an improved environmental health and safety (EH&S) profile over polyurethane products produced from isocyanates as well as improved hydrolytic and chemical stability.

The poly(hydroxyurethane) foam prepared as described herein may be used in the following end uses including for example, thermal insulation materials for exterior walls of building, roofing materials, refrigerators and freezers. Other uses of the poly(hydroxyurethane) foam of the present invention include construction sealants, packaging foams, structural foams simulated wood or other decorative structures.

In one embodiment, the poly(hydroxyurethane) foam is used for preparing a foam product.

In other embodiments, the present invention can include one or more processes including for example (i) a process for making a resin composition by admixing (a) the cyclic carbonate monomer compound of the present invention; and (b) an epoxy resin; (ii) a process for making a polymerizable composition by admixing (a) the cyclic carbonate monomer compound of the present invention; and (b) a carbonate co-reactive monomer; (iii) a process of making a polymerizable composition by admixing (a) the cyclic carbonate monomer compound of the present invention; and (b) a carbonate polymerization catalyst; (iv) a process of making a polymer by reacting (a) the cyclic carbonate monomer compound of the present invention; and (b) a carbonate co-reactive monomer; (v) a process for making a polymer by reacting (a) the cyclic carbonate monomer compound of the present invention; and (b) a carbonate polymerization catalyst; (vi) a process for making a foamable composition by admixing (a) the cyclic carbonate monomer compound of the present invention; and (b) a blowing agent; and (c) optionally, a surfactant; and (vii) a process of making a foam by reacting the above foamable composition.

In addition, the present invention includes an article made from a composition made by any of the above-mentioned processes.

EXAMPLES

The following chemicals and analytical methods were employed in the examples.

"DVBDC" stands for divinylbenzene dicyclic carbonate.

Divinylbenzene dioxide (DVBDO) has an epoxide equivalent weight (EEW)=81 g/eq.

D.E.R. 383 epoxy resin is a bisphenol A diglycidyl ether available from The Dow Chemical Company and has an EEW=180 g/eq.

Carbon dioxide is used in gaseous form from a pressurized cylinder.

Tetrabutylammonium bromide (TBAB) is available from Sigma-Aldrich and is used as a reaction catalyst.

Jeffamine T-403 and D-400 are polyetheramines available from Huntsman Advanced Materials and have amine hydrogen equivalent weights of 162 g/eq and 230 g/eq, respectively.

Triethylenetriamine (TETA) is a polyethyleneamine available from The Dow Chemical Company and has an amine hydrogen equivalent weight of 21 g/eq.

Surfactant L620 is a polysiloxane surfactant available from Momentive.

Percent carbonation is determined by $^1$H-NMR using a 300 MHz Brucker spectrometer.

Fourier-transform infrared (FTIR) analysis is done using a Nicolet Nexus 670 FT-IR spectrophotometer fitted with a Smart DuraSamplIR sample interface.

Melt viscosity ($\eta^*$) is determined using a TA Instruments ARES rheometer fitted with a 40 mm top and 50 mm bottom parallel plate fixture and operated using a temperature sweep from 100° C. to 25° C. for DVBDO materials and 200° C. to 25° C. for DER 383 materials at 5° C./minute and a frequency of 10 s$^{-1}$.

Glass transition temperature ($T_g$) is determined by differential scanning calorimetry (DSC) using a TA Instruments Q200 calorimeter operated using a temperature sweep at 10° C./minute.

Thermal decomposition temperature ($T_d$) is determined by thermogravimetric analysis (TGA) a TA Instruments Q50 Thermogravimetric Analyzer operated under nitrogen using a temperature sweep of 10° C./minute.

Examples 1-2 and Comparative Examples A-B

Preparation of Divinylbenzene Dicarbonate (DVBDC) and DER 383 Dicarbonate (DER 383-DC)

To a 500 mL, 4-necked round bottom flask fitted with a mechanical stirrer, a heating mantle, a thermocouple, and a gas inlet tube connected to a $CO_2$ cylinder were added the epoxy resin as shown in Table I and 0.8 g TBAB. The mixture was stirred and heated to 100° C. Then $CO_2$ at a cylinder pressure of 5 MPa with an outlet pressure of 0.03 MPa was added into the reaction mixture via the gas inlet tube. After the time indicated in Table I the gas addition was stopped and the resulting product was allowed to cool. FTIR analysis shows the presence of a carbonate band at 1780 cm$^{-1}$ in each product. $^1$H-NMR shows the disappearance of epoxide resonances and the appearance of carbonate resonances in each product.

TABLE I

Examples 1-2 and Comparative Examples A-B

| Example | Epoxy Resin | g | Time (hours) | % Carbonation | $\eta^*$ (150° C., Pa-s) |
|---|---|---|---|---|---|
| 1 | DVBDO | 250 | 84 | 100 | 40 |
| 2 | " | 250 | 20 | 74 | 20 |
| A | DER 383 | 300 | 30 | 100 | 153 |
| B | " | 300 | 9 | 50 | 242 |

Example 3

Preparation of 50% DVBDC (DVBDC-50)

To a sample of 10 g of DVBDC from Example 2 (DVBDC-74) was added 3.6 g of DVBDO to provide 13.6 g of DVBDC-50.

Examples 4-7 and Comparative Examples C-E

Preparation of Poly(hydroxyurethane)s from DVBDC or DER 383-DC from Polyamines

To a 20 mL vial were added the carbonate resin and amine in the amounts shown in Table II. The contents were mixed and cured at 100° C. for 24 hours. DSC and TGA analyses gave the $T_g$ and $T_d$ values shown in Table II.

TABLE II

Examples 4-7 and Comparative Examples C-E

| Example | Carbonate | g | Amine | g | $T_g$ (° C.) | $T_d$ (° C.) |
|---|---|---|---|---|---|---|
| 4 | DVBDC-74 | 2 | T-403 | 2.29 | 48 | 313 |
| 5 | " | 2 | TETA | 0.62 | 53 | 289 |
| 6 | " | 2 | D-400 | 3.03 | 3 | N/A |

TABLE II-continued

Examples 4-7 and Comparative Examples C-E

| Example | Carbonate | g | Amine | g | $T_g$ (° C.) | $T_d$ (° C.) |
|---|---|---|---|---|---|---|
| 7 | DVBDC-50 | 2 | T-403 | 2.35 | 46 | 260 |
| 8 | " | 2 | TETA | 0.71 | 90 | 280 |
| C | DER 383-DC-50 | 2 | T-403 | 1.05 | 50 | 300 |
| D | DER 383-DC-50 | 2 | TETA | 0.29 | 53 | 315 |
| E | DER 383-DC-50 | 2 | D-400 | 1.93 | 7 | N/A |

Example 8

Preparation of Poly(hydroxyurethane) Foam from DVBDC-74, TETA, and Cyclohexane To a 250 mL cup was added the following materials in order: 38.2 g DVBDC-74, 4.2 g cyclohexane, 1.9 g Surfactant L620, and 15.7 g TETA. The mixture was stirred using a high speed mixer for 10 seconds, poured into a 1 L container, and allowed to produce a poly(hydroxyurethane) foam having an approximate volume expansion of 10.

Example 9

Exothermic Behavior of Room Temperature-Cured Polymer from DVBDC-74 and TETA To a jacketed glass vial fitted with a thermocouple, 4 g of DVBDC-74 were added. Then, 1.24 g of TETA was added to the glass vial and the resulting mixture was mixed via a vortex mixer for 10 seconds. The temperature rise was measured giving an adiabatic temperature rise from room temperature (25° C.) to 125° C.

What is claimed:

1. A cyclic carbonate monomer comprising the reaction product of (a) a divinylarene dioxide; and (b) carbon dioxide, wherein the reaction product comprises divinylbiphenyl dicyclic carbonate, divinyl diphenyl ether dicyclic carbonate, bisphenol A dicyclic carbonate, bisphenol F dicyclic dicarbonate, or at least one compound having any one of the following chemical Structures VIII-X and XII:

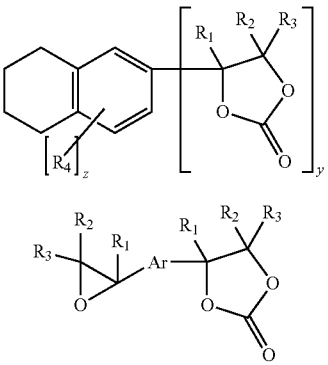

Structure VIII

Structure IX

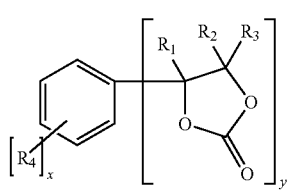

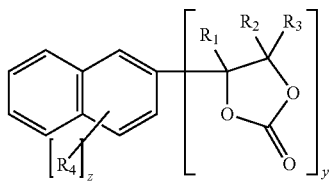

Structure X

Structure XII wherein in the above Structures VIII-X and XII, each $R_1$, $R_2$, and $R_3$ individually is hydrogen, an alkyl, cycloalkyl, an aryl or an aralkyl group; and each R4 individually is hydrogen, an alkyl, cycloalkyl, an aryl or an aralkyl group, a halogen, a nitro, an ester, an epoxy or an RO group, wherein R is an alkyl, aryl or aralkyl; x is an integer of 0 to 4; y is an integer greater than or equal to 2; x+y is an integer less than or equal to 6; z is an integer of 0 to 6; z+y is an integer less than or equal to 8; and Ar is an arene fragment.

2. The cyclic carbonate monomer of claim 1, wherein the reaction product comprises chemical Structure VIII.

3. The cyclic carbonate monomer of claim 2, wherein the reaction product is divinylbenzene dicyclic carbonate and is a mixture of ortho, meta, and para isomers.

4. The cyclic carbonate monomer of claim 2, wherein the reaction product is ethyl vinyl benzene monocyclic carbonate and is a mixture of ortho, meta, and para isomers.

5. The cyclic carbonate monomer of claim 1, wherein the reaction product comprises chemical structure IX.

6. The cyclic carbonate monomer of claim 5, wherein the reaction product is divinylnaphthalene dicyclic carbonate.

7. The cyclic carbonate monomer of claim 1, wherein the reaction product comprises chemical structure X.

8. The cyclic carbonate monomer of claim 1, wherein the reaction product is divinylbiphenyl dicyclic carbonate.

9. The cyclic carbonate monomer of claim 1, wherein the reaction product is divinyl diphenyl ether dicyclic carbonate.

10. The cyclic carbonate monomer of claim 1, wherein the reaction product is bisphenol A dicyclic carbonate.

11. The cyclic carbonate monomer of claim 1, wherein the reaction product is bisphenol F dicyclic dicarbonate.

12. The cyclic carbonate monomer of claim 1, wherein the reaction product comprises chemical structure XII.

13. The cyclic carbonate monomer of claim 12, wherein the reaction product is divinyl biphenyl mono oxide mono cyclic carbonate.

14. The cyclic carbonate monomer of claim 12, wherein the reaction product is divinyl diphenyl ether mono oxide mono cyclic carbonate.

15. The cyclic carbonate monomer of claim 12, wherein the reaction product is bisphenol A mono oxide monocyclic carbonate.

16. The cyclic carbonate monomer of claim 12, wherein the reaction product is bisphenol F mono oxide monocyclic carbonate.

* * * * *